United States Patent [19]

Caprathe et al.

[11] Patent Number: 5,409,931
[45] Date of Patent: Apr. 25, 1995

[54] 1,3-SUBSTITUTED CYCLOALKENES AND CYCLOALKANES AS CENTRAL NERVOUS SYSTEM AGENTS

[75] Inventors: Bradley W. Caprathe, Redford; Dennis M. Downing, Ann Arbor; Juan C. Jaen, Plymouth; Stephen J. Johnson, Ann Arbor; William J. Smith, III, Ann Arbor; Lawrence D. Wise, Ann Arbor; Jonathan Wright, Ann Arbor; David J. Wustrow, Ann Arbor, Mich.

[73] Assignee: Warner-Lambert Company, Morris Plains, N.J.

[21] Appl. No.: 192,238

[22] Filed: Feb. 4, 1994

Related U.S. Application Data

[60] Division of Ser. No. 957,277, Oct. 15, 1992, Pat. No. 5,314,896, which is a continuation-in-part of Ser. No. 795,207, Nov. 20, 1991, abandoned.

[51] Int. Cl.⁶ .............. A61K 31/495; A61K 31/50; C07D 403/00; C07D 401/00
[52] U.S. Cl. ..................... 514/252; 514/255; 544/295; 544/358; 544/360; 544/364; 544/369; 544/374; 544/379; 544/392; 544/398; 544/401; 544/405
[58] Field of Search ............... 544/360, 392, 333, 357, 544/295, 360, 364, 369, 374, 379, 358, 398, 401, 405, 392; 514/252, 255

[56] References Cited

U.S. PATENT DOCUMENTS

| 4,597,921 | 9/1990 | Caprathe et al. | 514/252 |
| 4,975,445 | 12/1990 | Caprathe et al. | 514/252 |
| 5,124,332 | 6/1992 | Wise et al. | 514/254 |

FOREIGN PATENT DOCUMENTS 345808  12/1989  European Pat. Off. .

*Primary Examiner*—Cecilia Tsang
*Attorney, Agent, or Firm*—Francis J. Tinney

[57] ABSTRACT 1,3-Substituted cycloalkenes and cycloalkanes are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

6 Claims, No Drawings

1,3-SUBSTITUTED CYCLOALKENES AND CYCLOALKANES AS CENTRAL NERVOUS SYSTEM AGENTS

This is a Divisional Application of U.S. Ser. No. 07/957,277 filed Oct. 15, 1992, now U.S. Pat. No. 5,314,896, which is a Continuation-in-part application of U.S. Ser. No. 07/795,207 filed Nov. 20, 1991, now abandoned.

BACKGROUND OF THE INVENTION

The present invention relates to novel substituted 1,3-cycloalkenes and cycloalkanes useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

A series of substituted cyclohexenes represented by the Formula I

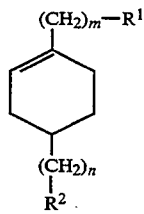

wherein $R^1$ is aryl, 2-, 3-, or 4-pyridinyl or 2-, 3- or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

m is zero or an integer from one to two;

$R^2$ is

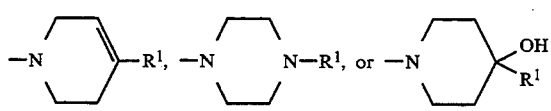

wherein $R^1$ is as defined above;

n is zero or an integer from one to four; and corresponding optical isomers thereof; or a pharmaceutically acceptable acid addition salt thereof, useful as dopaminergic agents, is disclosed in U.S. Pat. No. 4,975,445.

A series of 1-indolylalkyl-4-substituted pyridinyl piperazines represented by Formula I

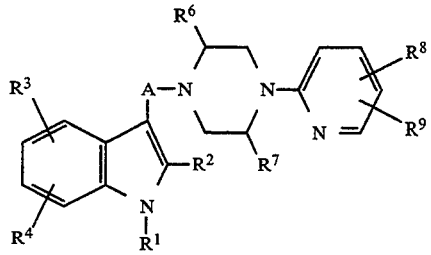

$R^1$, $R^2$ is H or 1–4C alkyl;

$R^3$, $R^4$, $R^8$, $R^9$ is H, lower alkyl, lower alkoxy, carbamide, halo, $CF_3$, or thio-lower alkyl; provided that $R^8$ and $R^9$ are not both H;

A is 5–7C cycloalkyl or cycloalkenyl, or —($CH_2$)$_n$—$CHR^5$—;

n is 1, 2, or 3;

$R^5$ is $R^1$;

$R^6$, $R^7$ is H or Me; or $R^4 + R^7$ is a methylene bridge or a pharmaceutically acceptable acid addition salt useful in the treatment of depression, anxiety, and panic disorders is disclosed in European Patent Application EP-345,808A.

However, the compounds disclosed in the aforementioned references do not disclose or suggest the combination of structural variations of the compounds of the present invention described hereinafter.

SUMMARY OF THE INVENTION

Accordingly, the present invention is a compound of Formula I $$Z-CH_2-Y \qquad I$$

wherein Z is

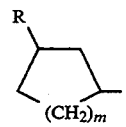

wherein R is aryl, 2-, 3-, or 4-pyridinyl or 2-, 3-, or 4-pyridinyl substituted by lower alkyl, lower alkoxy, hydroxy, or halogen, 2-, 4-, or 5-pyrimidinyl or 2-, 4-, or 5-pyrimidinyl substituted by lower alkyl, lower alkoxy, hydroxy, or halogen, 2-pyrazinyl or 2-pyrazinyl substituted by lower alkyl, lower alkoxy, hydroxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl, or 2-, 4-, or 5-thiazolyl substituted by lower alkyl or halogen, 3-indolyl, 2-, 3-, or 4-quinolinyl, and m is an integer of 1, 2, or 3,

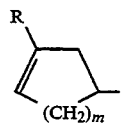

wherein R and m are as defined above,

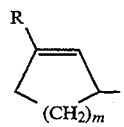

wherein R and m are as defined above, or

wherein R is as defined above;
Y is

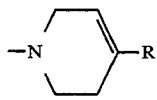

wherein R is as defined above or

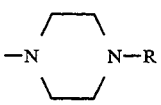

wherein R is as defined above; and corresponding isomers thereof; or a pharmaceutically acceptable acid addition salt thereof.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions such as galactorrhea, amenorrhea, menstrual disorders and sexual dysfunction, and several central nervous system disorders such as Parkinson's disease, and Huntington's chorea.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group, a phenyl group substituted by one to four substituents selected from lower alkyl, lower alkoxy, lower thioalkoxy, hydroxy, halogen, trifluoromethyl, amino, lower alkylamino or lower dialkylamino, or 1,3-benzodioxol-5-yL.

"Lower alkoxy" and "thioalkoxy" are O-alkyl or S-alkyl of from one to six carbon atoms as defined above for "lower alkyl".

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1–19 (1977) ).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention. Additionally, certain of the compounds of the present invention may exist as a mixture of cis and trans isomers or as the individual and trans isomers. The mixture of isomers as well as the individual isomers are intended to be encompassed within the scope of the present invention.

A preferred compound of Formula I is one wherein
R is phenyl, phenyl substituted by lower alkyl, lower alkoxy, lower dialkoxy, halogen, hydroxy, dihydroxy, amino, lower alkyl amino, lower dialkyl amino, 2- or 3-pyridyl, 2- or 3-pyridyl substituted by lower alkyl, lower alkoxy, or halogen, 2- or 3-thienyl, 2- or 3-thienyl substituted by lower alkyl, lower alkoxy, or halogen, 2-, 3- or 5-pyrimidinyl, 2-, 3-, or 4-quinolinyl, 3-indolyl, or

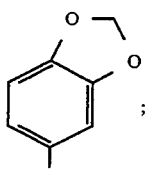

m is an integer of 1 or 2; and Y is

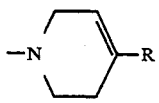

wherein R is as defined above.

Another preferred embodiment is a compound of Formula I wherein

R is phenyl, phenyl substituted by para-halogen, para-methoxy, ortho or para lower alkyl, para mono- or di-lower alkyl amino, 2- or 3-pyridyl, 2- or 3-thienyl, 5-pyrimidinyl, 3-quinolinyl, 3-indolyl or

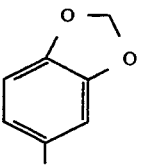

m is an integer of 2; and Y is

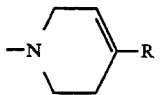

wherein R is as defined above.

Another preferred embodiment is a compound of Formula I wherein

R is phenyl, phenyl substituted by lower alkyl, lower alkoxy, lower dialkoxy, halogen, hydroxy, dihydroxy, amino, lower alkyl amino, lower dialkyl amino, 2- or 3-pyridyl, 2- or 3-pyridyl substituted by lower alkyl, lower alkoxy, or halogen, 2- or 3-thienyl, 2- or 3-thienyl substituted by lower alkyl, lower alkoxy, or halogen, 2-, 3- or 5-pyrimidinyl, 2-, 3- or 4-quinolinyl, 3-indolyl, or

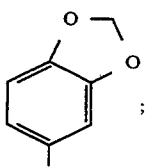

m is an integer of 1 or 2; and Y is

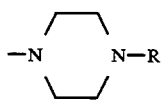

wherein R is as defined above.

Another preferred embodiment is a compound of Formula I wherein

R is phenyl, phenyl substituted by para-halogen, para-methoxy, ortho or para lower alkyl, para mono- or di-lower alkyl amino, 2- or 3-pyridyl, 2- or 3-thienyl, 5-pyrimidinyl, 3-quinolinyl, 3-indolyl or

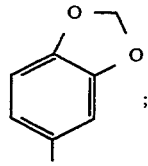

m is an integer of 2; and Y is

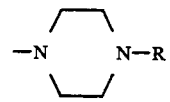

wherein R is as defined above.

Particularly valuable are:
(±)-1,2,3,6-Tetrahydro-4-phenyl-1-[(3-phenyl-3-cyclohexen-1-yl)methyl]pyridine;
(±)-1,2,3,6-Tetrahydro-4-phenyl-1-[(3-phenyl-2-cyclohexen-1-yl)methyl]pyridine;
(±)-1,2,3,6-Tetrahydro-4-phenyl-1-[[3-(2-thienyl)-3-cyclohexen-1-yl]methyl]pyridine;
(±)-1,2,3,6-Tetrahydro-4-phenyl-1-[[3-(2-thienyl)-2-cyclohexen-1-yl]methyl]pyridine;
(±)-1-[[3-(4-Fluorophenyl)-3-cyclohexen-1-yl]methyl]-1,2,3,6-tetrahydro-4-phenylpyridine;
(±)-1-[[3-(4-Fluorophenyl)-2-cyclohexen-1-yl]methyl-1,2,3,6-tetrahydro-4-phenylpyridine;
(±)-1-[(3-Phenyl-3-cyclohexen-1-yl)methyl]-4-(2-pyridinyl)piperazine;
(±)-1-[(3-Phenyl-2-cyclohexen-1-yl)methyl]-4-(2-pyridinyl)piperazine;
(±)-1-[[3-(4-Fluorophenyl)-3-cyclohexen-1-yl]methyl]-4-(2-pyridinyl)piperazine;
(±)-1-[[3-(4-Fluorophenyl)-2-cyclohexen-1-yl]methyl]-4-(2-pyridinyl)piperazine;
(+)-1,2,3,6-Tetrahydro-4-phenyl-1-[(3-phenyl-3-cyclohexen-1-yl)methyl]pyridine; and
(−)-1,2,3,6-Tetrahydro-4-phenyl-1-[(3-phenyl-3-cyclohexen-1-yl)methyl]pyridine;
(R)-1-[[3-(4-chlorophenyl)-3-cyclohexen-1-yl]methyl]-1,2,3,6-tetrahydro-4-phenylpyridine monohydrochloride;
(R)-1-[[3-(4-chlorophenyl)-2-cyclohexen-1-yl]methyl]-1,2,3,6-tetrahydro-4-phenylpyridine;
(R)-1-[[3-(4-fluorophenyl)-3-cyclohexen-1-yl]methyl]-1,2,3,6-tetrahydro-4-phenylpyridine;
(R)-1,2,3,6-tetrahydro-[3-(4-methylphenyl)-3-cyclohexen-1-yl]methyl-4-phenylpyridine;
(R)-1,2,3,6-tetrahydro-4-phenyl-1-[[3-(2-thienyl)-3-cyclohexen-1-yl]methyl]pyridine monohydrochloride;
(R)-1,2,3,6-tetrahydro-4-phenyl-1-[[3-(2-thienyl)-2-cyclohexen-1-yl]methyl]pyridine monohydrochloride;
(R)-1,2,3,6-tetrahydro-1-[[3-(4-methoxyphenyl)-3-cyclohexen-1-yl]methyl]-4-phenylpyridine monohydrochloride;
(R)-3-[5-[(3,6-dihydro-4-phenyl-1(2H)-pyridinyl)methyl]-1-cyclohexen-1-yl]pyridine monohydrochloride;

(R)-3-[3-[(3,6-dihydro-4-phenyl-1(2H)-pyridinyl)methyl]-1-cyclohexen-1-yl]pyridine dihydrochloride;

(R)-1,2,3,6- tetrahydro-1-[[3-(2-methylphenyl)-2-cyclohexen-1-yl]methyl]-4- phenylpyridine;

(R)-1,2,3,6-tetrahydro-1-[[3-(2-methylphenyl)-3-cyclohexen-1-yl]methyl]-4-phenylpyridine;

(R)-5-[5-[(3,6-dihydro-4-phenyl-1(2H)-pyridinyl)methyl]-1-cyclohexen-1-yl]pyrimidine monohydrochloride;

(R)-5-[3-[(3,6-dihydro-4-phenyl-1(2H)-pyridinyl)methyl]-1-cyclohexen-1-yl]pyrimidine dihydrochloride;

(R)-1,2,3,6-tetrahydro-4-phenyl -1-[[3-(3 -thienyl)-2-cyclohexen-1-yl]methyl]pyridine;

(R)-4-[5-[(3,6-dihydro-4-phenyl-1(2H)-pyridinyl)methyl]-1-cyclohexen-1-yl]- N,N-dimethylbenzeneamine;

(R)-4-[3-[(3,6-dihydro-4-phenyl-1(2H)-pyridinyl)methyl]-1-cyclohexen-1-yl]- N,N-dimethylbenzeneamine;

(R)-3-[5-[(3,6-dihydro-4-phenyl-1(2H)-pyridinyl)methyl]-1-cyclohexen-1-yl]quinoline;

(R)-3-[3-[(3,6-dihydro-4-phenyl-1(2H)-pyridinyl)methyl]-1- cyclohexen-1-yl]quinoline;

(R)-1-[[3-(1,3-benzodioxol-5-yl)-3-cyclohexen-1-yl]methyl]-1,2,3,6-tetrahydro-4-phenylpyridine monohydrochloride;

(1S-cis)-N-[3-[(3,6-dihydro-4-phenyl-l(2H)-pyridinyl)methyl]cyclohexyl]benzamide;

(1R-cis)-1,2,3,6-tetrahydro-4-phenyl-1-[(3-phenylcyclohexyl)methyl]pyridine monohydrochloride;

(1R-trans)-1,2,3,6-tetrahydro-4-phenyl-1-[(3-phenylcyclohexyl)methyl]pyridine monohydrochloride;

(R)-1-[(3-phenyl -3-cyclohexen-1-yl)methyl]-4-(2-pyridinyl)piperazine;

(±)-1-phenyl-4-[(3-phenyl-3-cyclohexen-1-yl)methyl]piperazine dihydrochloride;

(±)-2-[4-[[3-phenyl-3-cyclohexen-1-yl)methyl]-1-piperazinyl]pyrimidine;

(±)-1,2,3,6-tetrahydro-1-[(3-phenyl-3-cyclohexen-1-yl)methyl]-4-(2-thienyl)pyridine monohydrochloride;

(±)-1-[(3-phenyl-3-cyclopenten-1-yl)methyl]-4-(2 -pyridinyl)piperazine; and (±)-3-[5-[(3,6-dihydro-4-phenyl-1(2H)-pyridinyl)methyl]-1-cyclohexen-1-yl]-1H-indole; or a pharmaceutically acceptable acid addition salt thereof.

Most particularly valuable is: (+)-1,2,3,6-Tetrahydro-4-phenyl-1-[(3-phenyl-3-cyclohexen-1-yl)methyl]-pyridine.

The compounds of Formula I are valuable dopaminergic agents. The tests employed indicate that compounds of Formula I possess dopaminergic activity. Thus, the compounds of Formula I were tested for their ability to inhibit locomotor activity in mice and rats, a measure of antipsychotic activity, according to the assay described by J. R. McLean, et al, *Pharmacology, Biochemistry and Behavior*, Vol. 8, pages 97–99 (1978); for their ability to bind to dopamine receptors as measured by their inhibition of [$^3$H]spiroperidol binding in a receptor assay described by D. Grigoriadis and P. Seeman, *Journal of Neurochemistry*, Vol. 44, pages 1925–1935 (1985); and for their ability to effect dopamine synthesis in rats according to the protocol described by J. R. Walters and R. H. Roth, *Naunyn-Schmiedeberg's Archives of Pharmacology*, Vol. 296, pages 5–14 (1976). The above test methods are incorporated herein by reference. The data in the table show the dopaminergic activity of representative compounds of Formula I.

TABLE 1

Biological Activity of Compounds of Formula 1

| Example Number | Compound | Inhibition of Locomotor Activity in Mice ED$_{50}$, mg/kg, IP | % Effects on Brain Dopamine Synthesis in Rats at 10 mg/kg, IP | Inhibition of [$^3$H] Spiroperidol Binding IC$_{50}$, μM |
|---|---|---|---|---|
| 1 | (±)-1,2,3,6-Tetrahydro-4-phenyl-1-[(3-phenyl-3-cyclohexen-1-yl)methyl]pyridine | 1.6 | −86 | 0.152 |
| 1a | (±)-1,2,3,6-Tetrahydro-4-phenyl-1-[(3-phenyl-2-cyclohexen-1-yl)methyl]-pyridine | 2.5 | −34 | 0.420 |
| 2 | (±)-1,2,3,6-Tetrahydro-4-phenyl-1-[[3-(2-thienyl)-3-cyclohexen-1-yl]methyl]-pyridine | 1.8 | −9 | 0.202 |
| 2a | (±)-1,2,3,6-Tetrahydro-4-phenyl-1-[[3-(2-thienyl)-2-cyclohexen-1-yl]methyl]-pyridine | 2.3 | | 0.400 |
| 3 | (±)-1-[[3-(4-Fluorophenyl)-3-cyclohexen-1-yl]methyl]-1,2,3,6-tetrahydro-4-phenylpyridine | 4.2 | | 0.090 |
| 3a | (±)-1-[[3-(4-Fluorophenyl)-2-cyclohexen-1-yl]methyl]-1,2,3,6-tetrahydro-4-phenylpyridine | 2.9 | −41 | 1.073 |
| 4 | (±)-1-[(3-Phenyl-3-cyclohexen-1-yl)methyl]-4-(2-pyridinyl)piperazine | 0.85 | −61 | 0.141 |
| 4a | (±)-1-[(3-Phenyl-2-cyclohexen-1-yl)methyl]-4-(2-pyridinyl)piperazine | | | |
| 5 | (±)-1-[[3-(4-Fluorophenyl)-3-cyclohexen-1-yl]methyl]- | 1.2 | −58 | 0.143 |

TABLE 1-continued
Biological Activity of Compounds of Formula 1

| Example Number | Compound | Inhibition of Locomotor Activity in Mice ED$_{50}$, mg/kg, IP | % Effects on Brain Dopamine Synthesis in Rats at 10 mg/kg, IP | Inhibition of [$^3$H] Spiroperidol Binding IC$_{50}$, μM |
|---|---|---|---|---|
| | 4-(2-pyridinyl)piperazine | | | |
| 5a | (±)-1-[[3-(4-Fluorophenyl)-2-cyclohexen-1-yl]methyl]-4-(2-pyridinyl)piperazine | 2.2 | −48 | 0.279 |
| 6 | (+)-1,2,3,6-Tetrahydro-4-phenyl-1-[(3-phenyl-3-cyclohexen-1-yl)methyl]-pyridine | 1.0 | +50 | 0.227 |
| 6a | (−)-1,2,3,6-Tetrahydro-4-phenyl-1-[(3-phenyl-3-cyclohexen-1-yl)methyl]-pyridine | 5.6 | −34 | 0.420 |
| 7 | (R)-1-[[3-(4-chlorophenyl)-3-cyclohexen-1-yl]methyl]-1,2,3,6-tetrahydro-4-phenylpyridine monohydrochloride | 4.4 | −18 | 4.634 |
| 7a | (R)-1-[[3-(4-chlorophenyl)-2-cyclohexen-1-yl]methyl]-1,2,3,6-tetrahydro-4-phenylpyridine | 7.5 | | 2.321 |
| 8 | (R)-1-[[3-(4-fluorophenyl)-3-cyclohexen-1-yl]methyl]-1,2,3,6-tetrahydro-4-phenylpyridine | 4.0 | −74 | 0.076 |
| 9 | (R)-1,2,3,6-tetrahydro-1-[[3-(4-methylphenyl)-3-cyclohexen-1-yl]methyl]-4-phenylpyridine | 0.8 | −42 | 0.184 |
| 10 | (R)-1,2,3,6-tetrahydro-4-phenyl-1-[[3-(2-thienyl)-3-cyclohexen-1-yl]methyl]-pyridine monohydrochloride | 1.6 | −54 | 0.079 |
| 10a | (R)-1,2,3,6-tetrahydro-4-phenyl-1-[[3-(2-thienyl)-2-cyclohexen-1-yl]methyl]-pyridine monohydrochloride | 1.5 | −58 | 0.110 |
| 11 | (R)-1,2,3,6-tetrahydro-1-[[3-(4-methoxyphenyl)-3-cyclohexen-1-yl]methyl]-4-phenylpyridine monohydrochloride | 0.37 | −47 | 0.100 |
| 12 | (R)-3-[5-[(3,6-dihydro-4-phenyl-1(2H)-pyridinyl)-methyl]-1-cyclohexen-1-yl]pyridine monohydrochloride | 0.01 | −85 | 0.082 |
| 12a | (R)-3-[3-[(3,6-dihydro-4-phenyl-1(2H)-pyridinyl)-methyl]-1-cyclohexen-1-yl]pyridine dihydrochloride | 0.07 | −97 | 0.087 |
| 13 | (R)-1,2,3,6-tetrahydro-1-[[3-(2-methylphenyl)-2-cyclohexen-1-yl]methyl]-4-phenylpyridine monohydrochloride compound with (R)-1,2,3,6-tetrahydro-1-[[3-(2-methylphenyl)-3-cyclohexen-1-yl]methyl]-4-phenylpyridine | 2.3 | | |
| 14 | (R)-5-[5-[(3,6-dihydro-4-phenyl-1(2H)-pyridinyl)-methyl]-1-cyclohexen-1-yl]pyrimidine monohydrochloride | 0.4 | | 0.438 |
| 14a | (R)-5-[3-[(3,6-dihydro-4-phenyl-1(2H)-pyridinyl)-methyl]-1-cyclohexen-1-yl]pyrimidine dihydrochloride | 0.07 | | |
| 15 | (R)-1,2,3,6-tetrahydro-4-phenyl-1-[(3-(3-thienyl)-2-cyclohexen-1-yl]methyl]-pyridine | 1.3 | | 0.251 |
| 16 | (R)-4-[5-1(3,6-dihydro-4- | 0.2 | −76 | 0.053 |

TABLE 1-continued

Biological Activity of Compounds of Formula 1

| Example Number | Compound | Inhibition of Locomotor Activity in Mice $ED_{50}$, mg/kg, IP | % Effects on Brain Dopamine Synthesis in Rats at 10 mg/kg, IP | Inhibition of [$^3$H] Spiroperidol Binding $IC_{50}$, μM |
|---|---|---|---|---|
|  | phenyl-1(2H)-pyridinyl)-methyl]-1-cyclohexen-1-yl]-N,N-dimethylbenzeneamine |  |  |  |
| 16a | (R)-4-[3-[(3,6-dihydro-4-phenyl-1(2H)-pyridinyl)-methyl]-1-cyclohexen-1-yl]-N,N-dimethylbenzeneamine | 0.7 |  | 0.660 |
| 17 | (R)-3-[5-[(3,6-dihydro-4-phenyl-1(2H)-pyridinyl)-methyl]-1-cyclohexen-1-yl]quinoline | 0.23 | −21 | 0.076 |
| 17a | (R)-3-13-[(3,6-dihydro-4-phenyl-1(2H)-pyridinyl)-methyl]-1-cyclohexen-1-yl]quinoline | 1.7 |  | 1.108 |
| 18 | (R)-1-[[3-(1,3-benzodioxol-5-yl)-3-cyclohexen-1-yl]methyl]-1,2,3,6-tetrahydro-4-phenylpyridine monohydrochloride | 0.8 |  | 0.432 |
| 19 | (1S-cis)-N-[3-[(3,6-dihydro-4-phenyl-1(2H)-pyridinyl)methyl]-cyclohexyl]benzamide | 0.15 | −95 | 0.034 |
| 20 | (IR-cis)-1,2,3,6-tetrahydro-4-phenyl-1-[(3-phenylcyclohexyl)methyl]-pyridine monohydrochloride | 0.7 | −100 | 0.071 |
| 20a | (1R-trans)-1,2,3,6-tetrahydro-4-phenyl-1-[(3-phenylcyclohexyl)methyl]-pyridine monohydrochloride | 0.5 |  | 0.874 |
| 21 | (R)-1-[(3-phenyl-3-cyclohexen-1-yl)methyl]-4-(2-pyridinyl)piperazine | 9.9 | −27 | 0.076 |
| 22 | ([3S )-1-phenyl-4-[(3-phenyl-3-cyclohexen-1-yl)methyl]-piperazine dihydrochloride | 2.1 |  | 0.424 |
| 23 | (±)-2-[4-[[3-phenyl-3-cyclohexen-1-yl)methyl]-1-piperazinyl]pyrimidine | 8.5 |  | 0.354 |
| 24 | (±)-1,2,3,6-tetrahydro-1-[(3-phenyl-3-cyclohexen-1-yl)methyl]-4-(2-thienyl)-pyridine monohydrochloride | 1.5 |  | 0.170 |
| 25 | (±)-1-[(3-phenyl-3-cyclopenten-1-yl)methyl]-4-(2-pyridinyl)piperazine | 2.7 | −45 | 0.190 |
| 26 | (±)-3-15-[(3,6-dihydro-4-phenyl-1(2H)-pyridinyl)-methyl]-1-cyclohexen-1-yl]-1H-indole | 2.0 | −23 | 0.288 |

The data in Table 2 show a comparison between the activities of 1,3 substituted cyclohexene compounds, such as those disclosed in the present invention, and activities of 1,4 cyclohexene compounds, such as those disclosed in U.S, Pat. No. 4,975,445. Compounds A, B, and C are 1,4 cyclohexenes of formula:

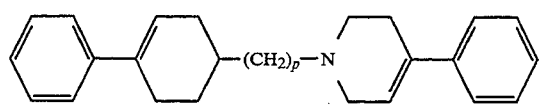

wherein p=0, 1, or 2 and the data in Table 2 show their binding and locomotor activity. Compounds D, 1, and E are 1,3 substituted cyclohexene compounds of formula:

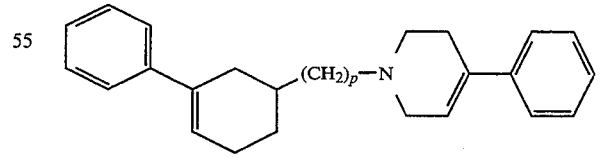

wherein p is as defined above. The data for these compounds show an unexpected trend. The 1,3 Compounds D and E, which correspond to the 1,4 Compounds A and C wherein p=0 or 2 show similar activity to the 1,4 compounds. The 1,3 cyclohexene Compound 1 with a single methylene spacer corresponding to m=1 is surprisingly much more active in its binding and locomotor activity. The most important test is the locomotor activity orally in the rat as this corresponds most closely to human oral administration of an antipsychotic compound. In this test, Compound 1 is clearly the most potent, being 4.8 times more active than the 1,4 Compound C.

Also the Compounds F, G and H are 1,4 substituted cyclohexenes of formula:

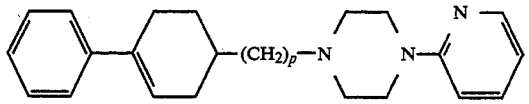

ing no methylene spacer (q=0) is essentially inactive, whereas Compound 4 having 1 methylene spacer (q=1) is very potent. This discovery is contrary to the teachings of the 1,4 series previously disclosed.

Thus, there are 2 unexpected features in the 1,3 cyclohexene series of the present invention when compared with the 1,4 cyclohexene series of U.S. Pat. No. 4,975,445. Firstly, activity is superior with the 1,3 substituted compounds. Secondly, activity is best in the 1,4 series when the number of methylene units in the spacer is 0 or 2. In the 1,3 series, activity resides almost exclusively in the compounds having 1 methylene spacer.

TABLE 2

Comparison of 1,2 versus 1,4 Series Activity

| Example Number | Compound | Inhibition of Locomotor Activity in Mice $ED_{50}$, mg/kg, IP | Inhibition of Locomotor Activity in Rats 10 mg/kg, PO | Inhibition of [$^3$H] Spiroperidol Binding $IC_{50}$, μM |
|---|---|---|---|---|
| A | (±)-1,2,3,6-tetrahydro-4-phenyl-1-(4-phenyl-3-cyclohexen-1-yl)pyridine | 12.9 | >30 | 1.080 |
| B | (±)-1,2,3,6-tetrahydro-4-phenyl-1-[(4-phenyl-3-cyclohexen-1-yl)methyl]-pyridine | 13.2 | 30 | 1.000 |
| C | (±)-1,2,3,6-tetrahydro-4-phenyl-1-[2-(4-phenyl-3-cyclohexen-1-yl)ethyl]-pyridine | 5.80 | 14.1 | 8.020 |
| D | (±)-1,2,3,6-tetrahydro-4-phenyl-1-(3-phenyl-3-cyclohexen-1-yl)pyridine | 30 | >30 | 9.207 |
| 1 | (±)-1,2,3,6-tetrahydro-4-phenyl-1-[(3-phenyl-3-cyclohexen-1-yl)methyl]-pyridine | 1.6 | 2.9 | 0.072 |
| E | (±)-1,2,3,6-tetrahydro-4-phenyl-1-[2-(3-phenyl-3-cyclohexen-1-yl)ethyl]-pyridine | 10.9 | >30 | 0.635 |
| F | (±)-1-(4-phenyl-3-cyclohexen-1-yl)-4-(2-pyridinyl)piperazine | 1.01 | >30 | 0.599 |
| G | (±)-1-[(4-phenyl-3-cyclohexen-1-yl)methyl]-4-(2-pyridinyl)piperazine | 25.9 | 30 | 11.240 |
| H | (±)-1-[(4-phenyl-3-cyclohexen-1-yl)ethyl]-4-(2-pyridinyl)piperazine | 1.10 | 6.7 | 0.409 |
| J | (±)-1-(3-phenyl-3-cyclohexen-1-yl)-4-(2-pyridinyl)piperazine | 28.2 | 30 | 9.847 |
| 4 | (±)-1-[(3-phenyl-3-cyclohexen-1-yl)methyl]-4-(2-pyridinyl)piperazine | 0.85 | 3.40 | 0.141 | wherein p=0, 1, or 2. The data clearly show that Compounds F and H are much more active than Compound G. Thus, this series teaches that activity is optimized when the number of methylenes in the spacer is 0 or 2 (ie, p=0 or 2). The Compounds J and 4 are 1,3 substituted cyclohexenes of formula:

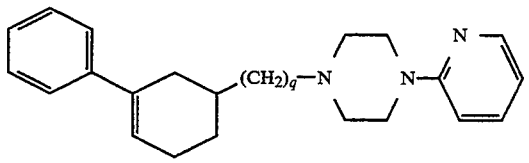

wherein q=0 or 1. Surprisingly and unexpectedly, the data for these compounds show that Compound J hav- A compound of Formula Ia $$Z^a—CH_2—Y \qquad Ia$$

wherein $Z^a$ is

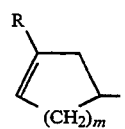

wherein R is aryl, 2-, 3-, or 4-pyridinyl or 2-, 3-, or 4-pyridinyl substituted by lower alkyl, lower alkoxy, hydroxy, or halogen, 2-, 4-, or 5-pyrimidinyl or 2-, 4-, or 5-pyrimidinyl substituted by lower alkyl, lower alkoxy, hydroxy, or halogen, 2-pyrazinyl or 2-pyrazinyl substituted by lower alkyl, lower alkoxy, hydroxy, or halogen, 2-, or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl, or 2-, 4-, or 5-thiazolyl substituted by lower alkyl or halogen, 3-indolyl, 2-, 3-, or 4-quinolinyl, and m is an integer of 1, 2, or 3, and

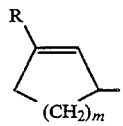

wherein R and m are as defined above;
Y is

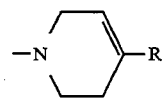

wherein R is as defined above or

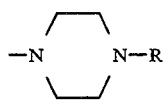

wherein R is as defined above; and corresponding isomers thereof;
or a pharmaceutically acceptable acid addition salt thereof may be prepared by reacting a compound of Formula II

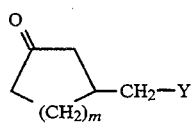  II wherein m and Y are as defined above with a compound of Formula III

R—M  III wherein M is Mg Hal wherein Hal is halogen or Li in a solvent such as, for example, tetrahydrofuran and the like at about 0° C. for about 30 minutes to about 2 hours followed by reaction with an acid such as, for example, trifluoroacetic acid in a solvent such as, for example, chloroform and the like at about room temperature for about 2 hours to about 24 hours to afford a compound of Formula Ia. Preferably, the reaction is carried out in tetrahydrofuran at about 0° C. for about 1 hour followed by reaction with trifluoroacetic acid in chloroform at about room temperature for about 18 hours.

A compound of Formula Ib $Z^b$—CH$_2$—$Y^a$  Ib wherein $Z^b$ is

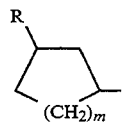

wherein R and m are as defined above;
$Y^a$ is

wherein R is as defined above; and corresponding isomers thereof; or a pharmaceutically acceptable acid addition salt thereof may be prepared by reacting a compound of Formula Ic $Z^a$—CH$_2$—$Y^a$  Ic wherein $Z^a$ and $Y^a$ are as defined above with hydrogen in the presence of a catalyst such as, for example, palladium on carbon and the like in a solvent such as, for example, methanol and the like to afford a compound of Formula Ib. Preferably, the reaction is carried out with palladium on carbon in methanol.

A compound of Formula Id $Z^b$—CH$_2$—Y  Id wherein $Z^b$ and Y are as defined above may be prepared by reacting a compound of Formula IV

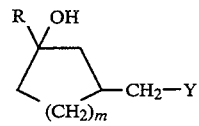  IV wherein R, m, and Y are as defined above with a reducing reagent such as, for example, triethylsilane in trifluoroacetic acid and the like to afford a compound of Formula Id. Preferably, the reaction is carried out with triethylsilane in trifluoroacetic acid.

A compound of Formula IV may be prepared by reacting a compound of Formula II with a compound of Formula III in a solvent such as, for example, tetrahydrofuran and the like at about 0° C. for about 30 minutes to about 2 hours to afford a compound of Formula IV. Preferably, the reaction is carried out in tetrahydrofuran at about 0° C. for about 1 hour. A compound of Formula II

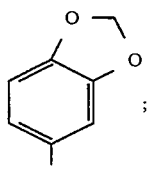

wherein m and Y are as defined above may be prepared from a compound of Formula V

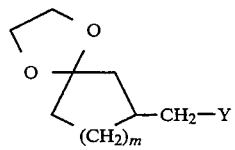  V wherein m and Y are as defined above by reaction with an acid such as, for example, hydrochloric acid and the like in a solvent such as, for example, acetone and the like to afford a compound of Formula II. Preferably, the reaction is carried out with dilute hydrochloric acid in acetone.

A compound of Formula V may be prepared from a compound of Formula VI

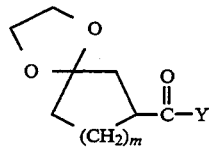

VI wherein m and Y are as defined above by reaction with a hydride reagent such as, for example, aluminum hydride and the like in a solvent such as, for example, tetrahydrofuran and the like to afford a compound of Formula V. Preferably, the reaction is carried out with aluminum hydride in tetrahydrofuran.

Alternatively, a compound of Formula V may be prepared from a compound of Formula VII

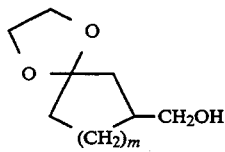

VII wherein m is as defined above by reaction with para-toluenesulfonyl chloride in the presence of a base such as, for example, pyridine and the like and subsequent reaction with a compound of Formula VIII

HY                     VIII wherein Y is as defined above to afford a compound of Formula V.

A compound of Formula VI may be prepared from a compound of Formula IX

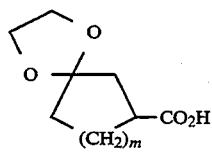

IX by reaction with thionyl chloride or ethyl chloroformate or isobutyl chloroformate and a compound of Formula VIII in the presence of a base such as, for example, triethylamine and the like in a solvent such as, for example, dichloromethane and the like at about 0° C. to about 30° C. for about 30 minutes to about 8 hours to afford a compound of Formula VI. Preferably, the reaction is carried out with isobutyl chloroformate in the presence of triethylamine in dichloromethane at about 25° C. for about 4 hours.

A compound of Formula VII may be prepared from a compound of Formula IX and a hydride reagent such as, for example, lithium aluminum hydride and the like in a solvent such as, for example, tetrahydrofuran and the like to afford a compound of Formula VII. Preferably, the reaction is carried out with lithium aluminum hydride in tetrahydrofuran.

A compound of Formula IX my be prepared from a compound of Formula X

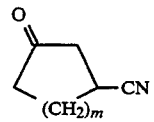

X wherein m is as defined above by reacting with an acid such as, for example, aqueous hydrochloric acid and the like and subsequent reaction with ethylene glycol in the presence of an acid such as, for example, para-toluenesulfonic acid and the like in a solvent such as, for example, benzene and the like to afford a compound of Formula IX. Preferably, the reaction is carried out with 10% aqueous hydrochloric acid solution and subsequent reaction with ethylene glycol in the presence of para-toluenesulfonic acid in benzene. Alternatively, a compound of Formula IV may be prepared from a compound of Formula XI

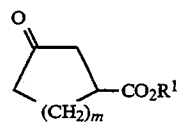

XI wherein $R^1$ is alkyl of from one to six carbon atoms and m is as defined above and a base such as, for example, an alkali metal hydroxide such as sodium or potassium hydroxide and subsequent reaction with ethylene glycol in the presence of para-toluenesulfonic acid in a solvent such as, for example, benzene and the like to afford a compound of Formula IX. Preferably, the reaction is carried out with sodium hydroxide and subsequent reaction with ethylene glycol in the presence of para-toluenesulfonic acid in benzene.

A compound of Formula X may be prepared from a compound of Formula XII

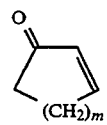

XII wherein m is as defined above by reaction with potassium cyanide in presence of an acid such as, for example, sulfuric acid and the like in water or reaction with trimethylsilyl cyanide in the presence of a Lewis acid such as, for example, zinc chloride and the like to afford a compound of Formula X. Preferably, the reaction is carried out with trimethylsilyl cyanide in the presence of zinc chloride.

A compound of Formula 1e

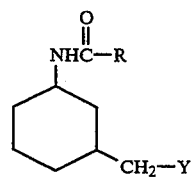

wherein R and Y are as defined above may be prepared by reacting a compound of Formula XIII

wherein R is as defined above with a compound of Formula XIV

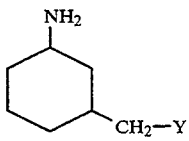

wherein Y is as defined above in the presence of a base such as triethylamine and the like in a solvent such as dichloromethane and the like at 0° C. to 50° C. for 1 to 72 hours. Preferably the reaction is carried out with triethylamine in dichloromethane at about 25° C. for about 24 hours.

A compound of Formula XIV may be prepared by reacting a compound of Formula II with a reducing agent in the presence of ammonium acetate and the like in a solvent such as an alcohol and the like at 0° C. to 50° C. for 1 to 72 hours. Preferably the reaction is carried out with sodium cyanoborohydride in methanol with ammonium acetate at about 25° C. for about 4 hours.

Compounds of Formula III, Formula VIII, Formula XI, Formula XII, and Formula XIII are either known or capable of being prepared by methods known in the art.

A compound of Formula I, which is a racemic mixture, may be further resolved into its enantiomers. Accordingly, as another aspect of the present invention, a compound of Formula (±)I may be resolved into its enantiomers by the use of conventional methodology such as, for example, optically active acids. Thus, the resulting diastereomeric salts may be separated by crystallization and then converted by conventional methodology to the optically active enantiomer (+)I or (−)I. For example, a compound of Formula (±)I is treated with (R)-(−)-1,1'-binaphthyl-2,2'-diyl hydrogen phosphate in a solvent such as, for example, acetonitrile and the like to afford the diastereomeric salt which is subsequently reacted with a base such as, for example, an alkali metal hydroxide, for example, sodium hydroxide to afford a compound of Formula (+)I. A compound of Formula (−)I is obtained from a compound of Formula (±)I by substituting (S)-(+)-1,1'-binaphthyl-2,2'-diyl hydrogen phosphate for (R)-(−)-1,1'-binaphthyl-2,2'-diyl hydrogen phosphate and using the previous methodology.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, Formula XV, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

($\pm$)-1,2,3,6-Tetrahydro-4-phenyl-1-[(3-phenyl-3-cyclohexen-1-yl)methyl]pyridine and

EXAMPLE 1a ($\pm$)-1,2,3,6-Tetrahydro-4-phenyl-1-[(3-phenyl-2-cyclohexen-1-yl)methyl]pyridine To a solution of 3-[(3,6-dihydro-4-phenyl-1(2H)-pyridinyl)methyl]cyclohexanone (Example A) (5.9 g) in 400 mL of tetrahydrofuran is added a solution of phenylmagnesium bromide (9.13 mL, 3.0M in diethyl ether), dropwise under nitrogen, at 0° C. The mixture is stirred at room temperature for 1 hour, then cooled in an ice bath and quenched with 250 mL of 10% aqueous hydrochloric acid solution. The solvent is evaporated in vacuo and the residue partitioned into chloroform/5% aqueous ammonium hydroxide solution. The organic extract is dried over magnesium sulfate and filtered. The filtrate is treated with trifluoroacetic acid (4.2 mL) and stirred overnight at room temperature. The solvent is evaporated in vacuo, and the residue is partitioned into ethyl acetate/5% aqueous ammonium hydroxide solution. The organic extract is dried over magnesium sulfate, filtered, and concentrated. The crude product is purified by medium pressure chromatography to give 3.9 g of ($\pm$)-1,2,3,6-tetrahydro-4-phenyl-1-[(3-phenyl-3-cyclohexen-1-yl)methyl]pyridine; mp 90°–95° C. as an off-white solid (Example 1) and 2.7 g of ($\pm$)-1,2,3,6-tetrahydro-4-phenyl-1-[(3-phenyl-2-cyclohexen-1-yl) methyl]pyridine; mp 124°–126° C. as a tan solid (Example 1a).

In a process analogous to Example 1 and 1a using appropriate starting materials, the corresponding compounds of Formula I are prepared as follows:

EXAMPLE 2

($\pm$)-1,2,3,6-Tetrahydro-4-phenyl-1-[[3-(2-thienyl)-3-cyclohexen-1-yl]methyl]pyridine; mp 97°–99° C. as a tan solid and

EXAMPLE 2a ($\pm$)-1,2,3,6-Tetrahydro-4-phenyl-1-[[3-(2-thienyl)-2-cyclohexen-1-yl]methyl]pyridine; mp 123°–127° C. as an off-white solid.

EXAMPLE 3

($\pm$)-1-[[3-(4-Fluorophenyl)-3-cyclohexen-1-yl]methyl]-1,2,3,6-tetrahydro-4-phenylpyridine; mp 116°–120° C. as an off-white solid and

EXAMPLE 3a ($\pm$)-1-[[3-(4-Fluorophenyl)-2-cyclohexen-1-yl]methyl]-1,2,3,6-tetrahydro-4-phenylpyridine; mp 159°–162° C. as a light yellow solid.

EXAMPLE 4

($\pm$)-1-[(3-Phenyl-3-cyclohexen-1-yl) methyl]-4-(2-pyridinyl)piperazine and

EXAMPLE 4a ($\pm$)-1-[(3-Phenyl-2-cyclohexen-1-yl)methyl]-4-(2-pyridinyl)piperazine To a solution of 5.14 g of 3-[[4-(2-pyridinyl)piperazinyl]methyl]cyclohexanone (Example B) in 250 mL of tetrahydrofuran at 0° C. under nitrogen is added dropwise a solution of phenyllithium (23.5 mL, 2.0M in cyclohexane/diethyl ether, 70/30). The solution is stirred at 0° C. for 1 hour, quenched with dropwise addition of 250 mL of saturated potassium phosphate monobasic solution. The solvent is evaporated in vacuo, the residue is basified with concentrated ammonium hydroxide to a pH of 9 and extracted into chloroform. The chloroform extract is dried over magnesium sulfate and filtered. A solution of the filtrate in 250 mL of chloroform containing 14.5 mL of trifluoroacetic acid is stirred at room temperature under nitrogen for 12 hours. The solvent is evaporated in vacuo, the residue is dissolved into ethyl acetate (250 mL) and washed with 1N sodium hydroxide solution and brine (250 mL of each). The ethyl acetate extract is dried over magnesium sulfate, filtered, and concentrated. The crude product is purified by medium pressure chromatography (silica gel, 90% hexanes - 10% ethyl acetate) to give ($\pm$)-1-[(3-phenyl-3-cyclohexen-1-yl)methyl]-4-(2-pyridinyl)piperazine (Example 4) as an off-white solid; mp 96°–98° C. and ($\pm$)-1-[(3-phenyl-2-cyclohexen-1-yl)methyl]-4-(2-pyridinyl)piperazine (Example 4a) as an off-white solid; mp 78°–82° C.

In a process analogous to Example 4 and 4a using appropriate starting materials, the corresponding compounds of Formula I are prepared as follows:

EXAMPLE 5

($\pm$)-1-[[3-(4-Fluorophenyl)-3-cyclohexen-1-yl]methyl]-4-(2-pyridinyl)piperazine; mp 116°–118° C. as an off-white solid and

EXAMPLE 5a ($\pm$)-1-[[3-(4-Fluorophenyl)-2-cyclohexen-1-yl]methyl]-4-(2--pyridinyl)piperazine; mp 129°–133° C. as a white solid.

EXAMPLE 6

(+)-1,2,3,6-Tetrahydro-4-phenyl-1-(3-phenyl-3-cyclohexen-1-yl]methyl]pyridine

A solution of ($\pm$)-1,2,3,6-tetrahydro-4-phenyl-1-[(3-phenyl-3-cyclohexen-1-yl)methyl]pyridine (5.31 g, Example 1) in 50 mL of acetonitrile is treated with a solution of (R)-(−)-1,1'-binaphthyl-2,2'-diyl hydrogen phosphate (4.21 g, Aldrich) in 50 mL of ethanol: methylene chloride (1:1). The volume of solution is reduced to ca 50 mL by boiling on a steam bath. Upon cooling, an off-white solid forms. The salt is recrystallized twice from 95% ethanol to yield 5.11 g of a white solid, mp 227°–234° C. The salt is partitioned between chloroform and 10% aqueous sodium hydroxide solution. The mixture is filtered through a pad of diatomaceous earth (Celite) and the layers are separated. The organic extract is dried over magnesium sulfate, filtered, and evaporated in vacuo to give (+)-1,2,3,6-tetrahydro-4-phenyl-1-[(3-phenyl-3-cyclohexen-1-yl)methyl]pyridine as an off-white solid; mp 94°–96° C., $[\alpha]_D$ +60.4° (c=1.12, chloroform).

EXAMPLE 6a (−)-1,2,3,6-Tetrahydro-4-phenyl-1-[(3-phenyl-3-cyclohexen-1-yl)methyl]pyridine In a process analogous to Example 6 by substituting (S)-(+)-1,1′-binaphthyl-2,2′-diyl hydrogen phosphate for (R)-(−)-1,1′-binaphthyl-2,2′-diyl hydrogen phosphate the title compound can be obtained as an off-white solid; mp 94°–100° C., $[\alpha]_D$ −63.7°(c=1.095, chloroform).

EXAMPLE 7

(R)-1-[[3-(4-chlorophenyl)-3-cyclohexen-1-yl]methyl]-1,2,3,6-tetrahydro-4-phenylpyridine and

EXAMPLE 7a (R)-1-[[3-(4-chlorophenyl)-2-cyclohexen-1-yl]methyl]-1,2,3,6-tetrahydro-4-phenylpyridine (R)-1,2,3,6-Tetrahydro-4-phenyl-1-[(3-oxocyclohexane)methyl]pyridine (Example C) (1.50 g) in tetrahydrofuran (40 mL) is added dropwise to 4-chlorophenylmagnesium bromide (11.1 mL of 1.0M in ether) in ether (30 mL) at 0° C. under nitrogen and stirred for 1 hour. Saturated aqueous ammonium chloride (100 mL) is added, the organic layer washed with brine (100 mL), dried over magnesium sulfate, filtered, and evaporated to leave a yellow foam (2.41 g). This foam is dissolved in 1,2-dichloroethane (100 mL) and trifluoroacetic acid (2.14 mL) and stirred at reflux for 1 hour. The solvent is evaporated and the residue treated with 2N sodium carbonate (100 mL). The mixture is extracted with dichloromethane (2×75 mL), the extracts washed with brine (75 mL), dried over magnesium sulfate, filtered, and evaporated to a white solid. This solid is purified by column chromatography on silica gel eluting with 5%, then 7% ethyl acetate/hexane to give (R)-1-[[3-(4-chlorophenyl)-2-cyclohexen-1-yl]methyl]-1,2,3,6-tetrahydro-4-phenylpyridine (0.875 g) as off-white solid; mp 157°–161° C. and (R)-1-[[3-(4-chlorophenyl)-3-cyclohexen-1-yl]methyl]-1,2,3,6-tetrahydro-4-phenylpyridine (0.875 g) as off-white solid; mp 138°–141° C.

In a process analogous to Example 7 using the appropriate starting materials, the corresponding compounds of Formula I are prepared as follows:

EXAMPLE 8

(R)-1-[[3-(4-fluorophenyl)-3-cyclohexen-1-yl]methyl]-1,2,3,6-tetrahydro-4-phenylpyridine; mp 130°–132° C. as a white solid.

EXAMPLE 9

(R)-1,2,3,6-tetrahydro-1-[[3-(4-methylphenyl)-3-cyclohexen-1-yl]methyl]-4-phenylpyridine; mp 101.5°–103.5° C. as a white solid.

EXAMPLE 10

(R)-1,2,3,6-tetrahydro-4-phenyl-1-[[3-(2-thienyl)-3-cyclohexen-1-yl]methyl]pyridine monohydrochloride; mp 223°–225° C. as a white solid, and

EXAMPLE 10a (R)-1,2,3,6-tetrahydro-4-phenyl-1-[[3-(2-thienyl)-2-cyclohexen-1-yl]methyl]pyridine monohydrochloride; mp 227°–230° C. as a white solid.

EXAMPLE 11

(R)-1,2,3,6-tetrahydro-1-[[3-(4-methoxyphenyl)-3-cyclohexen-1-yl]methyl]-4-phenylpyridine monohydrochloride; mp 201°–205° C. as a white solid.

EXAMPLE 12

(R)-3-[5-[(3,6-dihydro-4-phenyl-1(2H)-pyridinyl)methyl]-1-cyclohexen-1-yl]pyridine monohydrochloride; mp 135°–140° C. as a white solid, and

EXAMPLE 12a (R)-3-[3-[(3,6-dihydro-4-phenyl-1(2H)-pyridinyl)methyl]-1-cyclohexen-1-yl]pyridine dihydrochloride; mp 249°–253° C. as a white solid.

EXAMPLE 13

(R)-1,2,3,6-tetrahydro-1-[[3-(2-methylphenyl)-2-cyclohexen-1-yl]methyl]-4-phenylpyridine and (R)-1,2,3,6-tetrahydro-1-[[3-(2-methylphenyl)-3-cyclohexen-1-yl]methyl]-4-phenylpyridine, 2:1 mixture monohydrochloride; mp 213°–215° C. as a white solid.

EXAMPLE 14

(R)-5-[5-[(3,6-dihydro-4-phenyl-1(2H)-pyridinyl)methyl]-1-cyclohexen-1-yl]pyrimidine monohydrochloride; mp 192°–194° C. as a white solid, and

EXAMPLE 14a (R)-5-[3-[(3,6-dihydro-4-phenyl-1(2H)-pyridinyl)methyl]-1-cyclohexen-1-yl]pyrimidine dihydrochloride; mp >220° C. as a white solid.

EXAMPLE 15

(R)-1,2,3,6-tetrahydro-4-phenyl-1-[[3-(3-thienyl)-2-cyclohexen-1-yl]methyl]pyridine; mp 126°–128° C. as a white solid.

EXAMPLE 16

(R)-4-[5-[(3,6-dihydro-4-phenyl-1(2H)-pyridinyl)methyl]-1-cyclohexen-1-yl]-N,N-dimethylbenzeneamine; mp 126°–127° C. as a white solid, and

EXAMPLE 16 a (R)-4-[3-[(3,6-dihydro-4-phenyl-1(2H)-pyridinyl)methyl]-1-cyclohexen-1-yl]-N,N-dimethylbenzeneamine; mp 158°–160° C. as a white solid.

EXAMPLE 17

(R)-3-[5-[(3,6-dihydro-4-phenyl-1(2H)-pyridinyl)methyl]-1-cyclohexen-1-yl]-quinoline; mp 120°–123° C. as a white solid, and

EXAMPLE 17a (R)-3-[3-[(3,6-dihydro-4-phenyl-1(2H)-pyridinyl)methyl]-1-cyclohexen-1-yl]-quinoline; mp 134°–136° C. as a white solid.

EXAMPLE 18

(R)-1-[[3-(1,3-benzodioxol-5-yl)-3-cyclohexen-1-yl]methyl]-1,2,3,6-tetrahydro-4-phenylpyridine monohydrochloride; mp 210°–212° C. as a white solid.

EXAMPLE 19

(1S-cis)-N-[3-[(3,6-dihydro-4-phenyl-1(2H)-pyridinyl)methyl]cyclohexyl]benzamide A mixture of (R)-1,2,3,6-Tetrahydro-4-phenyl-1-[(3-oxocyclohexane)methyl]pyridine (Example C) (2.00 g), ammonium acetate (5.72 g) and sodium cyanoborohydride (0.311 g) in methanol (40 mL) is stirred at 25° C. for 2 hours. The solvent is evaporated and the residue treated with 2N sodium carbonate (100 mL) and extracted with dichloromethane (3×100 mL). The extracts are washed with brine (200 mL), dried over magnesium sulfate, filtered, and evaporated to leave a yellow oil. This oil is purified by medium pressure liquid chromatography on silica gel eluting with 40:8:1 dichloromethane:ethanol:ammonium hydroxide to give a yellow oil. A mixture of the oil, triethylamine (0.753 mL), benzyl chloride (0.684 mL) and 4-(N,N-dimethylamino)pyridine (50 mg) in dichloromethane (100 mL) is stirred at 25° C. for 3 hours. 2N Sodium carbonate (100 mL) is added and the organic layer separated, dried over magnesium sulfate, filtered, and evaporated to leave a yellow solid. This solid is purified by medium pressure liquid chromatography on silica gel eluting with 3% methanol in dichloromethane to give 0.62 g of (1S-cis)-N-[3-[(3,6-dihydro-4-phenyl-1(2H)-pyridinyl)methyl]cyclohexyl]benzamide as a white solid; mp 200°–204° C.

EXAMPLE 20

(1R-Cis)-1,2,3,6-tetrahydro-4-phenyl-1-[(3-phenylcyclohexyl)methyl]pyridine monohydrochloride and

EXAMPLE 20a (1R-Trans)-1,2,3,6-tetrahydro-4-phenyl-1-[(3-phenylcyclohexyl)methyl]pyridine monohydrochloride (R)-3-phenyl-3-cyclohexenecarboxylic acid (0.75 g, Example D) is hydrogenated in isopropanol (75 mL) with 10% palladium-on-carbon (0.1 g) at 50 psi for 24 hours. The mixture is filtered and evaporated to leave a colorless oil. Dicyclohexylcarbodiimide (0.839 g) in dichloromethane (10 mL) is added to a mixture of this oil, 1,2,3,6-tetrahydro-4-phenylpyridine hydrochloride (0.796 g), hydroxybenzotriazole hydrate (0.549 g) and triethylamine (1.13 mL) in dichloromethane (20 mL) and stirred overnight. The mixture is filtered, washed with 2N hydrochloric acid (2×100 mL), 2N sodium carbonate (100 mL), brine (100 mL), dried over magnesium sulfate, filtered, and evaporated to leave a yellow oil. This oil is purified by column chromatography on silica gel (TLC grade) eluting with 60% to 100% ethyl acetate in hexane to give 0.325 g of a colorless oil and 0.692 g of the other isomer as a waxy solid. This solid is dissolved in tetrahydrofuran (5 mL) and added to lithium aluminum hydride (75 mg) in tetrahydrofuran (2 mL) pretreated with aluminum chloride (87 mg) in ether (2 mL) at 0° C. and stirred for 1 hour. Water (90 μL) and 25% sodium hydroxide (0.38 mL) are added and the mixture filtered and evaporated to a yellow oil. This oil is purified by medium pressure liquid chromatography on silica gel eluting with 10% ethyl acetate in hexane to give a yellow oil. This oil is dissolved in ether (10 mL) and ethanol (2 mL) and 1M hydrogen chloride in ether (1.46 mL) added. The salt is collected, washed with ether, and dried at 50° C. under high vacuum to give 0.498 g of (1R-cis)-1,2,3,6-tetrahydro-4-phenyl-1-[(3-phenylcyclohexyl)methyl]pyridine monohydrochloride as an off-white solid; mp 200°–202° C. In a similar manner, the other isomer was reduced and the salt formed to give 0.152 g of (1R-trans)-1,2,3,6-tetrahydro-4-phenyl-1-[(3-phenylcyclohexyl)methyl]pyridine monohydrochloride as a white solid; mp 231°–235° C.

EXAMPLE 21

(R)-1-[(3-Phenyl-3-cyclohexen-1-yl)methyl]-4-(2-pyridiyl)piperazine

Dicyclohexylcarbodiimide (0.506 g) in dichloromethane (10 mL) is added to (R)-3-phenyl-3-cyclohexenecarboxylic acid (0.414 g, Example D), 2-pyridylpiperazine (0.410 g) and hydroxybenzotriazole hydrate (0.332 g) in dichloromethane (40 mL) and stirred overnight. The mixture is filtered and evaporated. The residue is dissolved in ethyl acetate, filtered, washed with saturated sodium bicarbonate, 5% citric acid, 2N sodium carbonate, brine, dried over magnesium sulfate, filtered, and evaporated to leave a yellow solid. This solid is dissolved in tetrahydrofuran (5 mL) and added to lithium aluminum hydride (78 mg) in tetrahydrofuran (5 mL) pretreated with aluminum chloride (90 mg) in ether (5 mL) at 0° C. and stirred for 2 hours. Water (0.1 mL) and 25% sodium hydroxide (0.4 mL) are added and the mixture filtered, washed with brine, dried over magnesium sulfate, filtered, and evaporated to a yellow oil. This oil is purified by medium pressure liquid chromatography on silica gel eluting with 50% ethyl acetate in hexane to give 0.22 g of (R)-1-[(3-Phenyl-3-cyclohexen-1-yl)methyl]-4-(2-pyridinyl)piperazine as an off-white solid; mp 106°–108° C.

EXAMPLE 22

(±)-1-Phenyl-4-[(3-phenyl-3-cyclohexen-1-yl)methyl]piperazine dihydrochloride

A solution of 3-phenyl-3-cyclohexenyl carboxylic acid (0.75 g, Example D), 1-phenylpiperazine (0.66 g), hydroxybenzotriazole hydrate (0.55 g) and triethylamine (0.57 mL) in dichloromethane (10 mL) is cooled to 0° C., treated with dicyclohexylcarbodiimide (0.84 g), and stirred for 1 hour at 0° C. and then at 25° C. overnight. The mixture is filtered, washed with 1N hydrochloric acid (2×100 mL), saturated sodium bicarbonate solution (100 mL), dried over sodium sulfate, filtered, and evaporated to leave a yellow oil. This oil is purified by column chromatography on silica gel (230–400 mesh) eluting with 1:4 ethyl acetate: chloroform to give 1.0 g of the amide as a white solid. This solid is dissolved in tetrahydrofuran (5 mL) and added to lithium aluminum hydride (0.33 g) in tetrahydrofuran (20 mL) pretreated with aluminum chloride (0.33 g) in ether (20 mL) at 0° C. and the reaction was allowed to come to 25° C. over 3 hours. The reaction is cooled in an ice bath and water (2 mL) is carefully added followed by 10% sodium hydroxide (4 mL) and the mixture is stirred at 25° C. for 2 hours. The mixture is filtered through celite and evaporated to a white solid. This solid is dissolved in ether (30 mL), filtered, and 1M hydrogen chloride in ether (3 mL) added. The salt is collected, washed with ether, and dried at 50° C. under high vacuum to give 0.88 g of (±)-1-phenyl-4-[(3-phenyl-3-cyclohexen-1-yl)methyl]piperazine dihydrochloride as an off-white solid; mp 212°–214° C.

In a process analogous to Example 22 using the appropriate starting materials, the corresponding compounds of Formula I are prepared as follows:

EXAMPLE 23

(±)-2-[4-[[3-phenyl-3-cyclohexen-1-yl)methyl]-1-piperazinyl]pyrimidine; mp 68°-70° C. as a white solid.

EXAMPLE 24

Using 1,2,3,6-tetrahydro-4-(2-thienyl)pyridine (EP 0175 541 A1), (±)-1,2,3,6-tetrahydro-1-[(3-phenyl-3-cyclohexen-1-yl)methyl]-4-(2-thienyl)pyridine monohydrochloride; mp 238°-240° C. as a white solid.

EXAMPLE 25

(±)-1-[(3-phenyl-3-cyclopenten-1-yl)methyl]-4-(2-pyridinyl)piperazine

This compound is prepared using 3-phenyl-3-cyclopentenecarboxylic acid which is prepared in Example E to give (±)-1-[(3-phenyl-3-cyclopenten-1-yl)methyl]-4-(2-pyridinyl)piperazine as a white solid; mp 100°-101° C.

EXAMPLE 26

(±)-3- [5-[(3,6-dihydro-4-phenyl-1(2H)-pyridinyl)-methyl]-1-cyclohexen-1-yl]-1H-indole A mixture of 3-phenyl-3-cyclohexenecarboxylic acid (1.00 g, Example D), indole (0.48 g), and sodium methoxide (1.20 g) in methanol (10 mL) is heated to reflux for 60 hours under nitrogen. The reaction mixture is concentrated to half of its original volume. The resulting slurry is filtered, the solid collected dissolved in chloroform, and purified by medium pressure liquid chromatography on silica gel eluting with 95:5:0.1 chloroform:methanol:ammonium hydroxide to give 0.21 g of (±)-3-[5-[(3,6-dihydro-4-phenyl-1(2H)-pyridinyl)methyl]-1-cyclohexen-1-yl]-1H-indole as an off-white solid; mp 174° C.

PREPARATION OF STARTING MATERIALS

EXAMPLE A

3-[(3,6-Dihydro-4-phenyl-1(2H)-pyridinyl)methyl]-cyclohexanone

Step A: Preparation of 1,4-Dioxaspiro[4.5]decane-7-carboxylic acid

A mixture of ethyl 3-oxocyclohexanecarboxylate (Nallet, J- P., et al, *Bull. Soc. Chem. Fr.*, Part II, No. 3–4, pages 153–156 (1979)) (101.7 g) ethylene glycol (38.9 g) and para-toluenesulfonic acid (5.5 g) in 1000 mL of benzene is refluxed with a Dean-Stark trap for 4 hours. The solution is cooled, washed with 1N sodium hydroxide and brine, dried over magnesium sulfate, and evaporated in vacuo to give 113.1 g of a light oil which is dissolved in 1000 mL of ethanol, treated with sodium hydroxide (25.3 g) in 250 mL of water, and refluxed for 2.5 hours. The mixture is concentrated in vacuo, cooled in an ice bath, and acidified with ice-cold 1N aqueous hydrochloric acid solution to a pH of 2. The title compound is extracted with chloroform (2×500 mL), dried over magnesium sulfate, and concentrated in vacuo. The title compound (99.3 g) is obtained as a yellowish oil, which is determined to be 98% pure by gas chromatography and is carried on without further purification.

Step B: Preparation of 1-(1,4-Dioxaspiro[4.5]dec-7-ylcarbonyl)-1,2,3,6-tetrahydro-4-phenylpyridine A solution of 1,4-dioxaspiro[4.5]decane-7-carboxylic acid (Step A) (99.3 g) and triethylamine (80.8 g) in 1000 mL of dichloromethane is cooled in an ice bath, and treated dropwise with isobutyl chloroformate (80.1 g), dropwise, under nitrogen. After 30 minutes, a solution of 4-phenyl-1,2,3,6-tetrahydropyridine (84.7 g) in 500 mL of dichloromethane is added dropwise over a 2-hour period. The mixture is stirred at room temperature for 2 additional hours. The solvent is removed in vacuo. The residue is suspended in 1000 mL of ethyl acetate, cooled to 0° C., and sequentially washed with ice-cold 1N aqueous hydrochloric acid solution and brine, dried over magnesium sulfate, and evaporated in vacuo. The crude product is purified by flash chromatography (silica; hexane:ethyl acetate, 3:1) to give 107.1 g of the title compound as a yellow oil (silica; $R_f$=0.4; 1% methanol, 99% chloroform); Mass Spectrum (Electron Ionization) (MS (EI)) 327 (M, 26.1%), 141 (100%).

Step C: Preparation of 1-(1,4-Dioxaspiro[4.5]dec-7-yl methyl)-1,2,3,6-tetrahydro-4-phenylpyridine A solution of aluminum chloride (14.54 g) in 500 mL of anhydrous diethyl ether is added dropwise to a suspension of lithium aluminum hydride (12.41 g) in 500 mL of tetrahydrofuran. The mixture is stirred at room temperature for 30 minutes. A solution of 1-(1,4-dioxaspiro[4.5]dec-7-yl carbonyl)-1,2,3,6-tetrahydro-4-phenylpyridine (Step B) in 500 mL of tetrahydrofuran is added dropwise. The mixture is stirred at room temperature overnight, and it is quenched by careful addition of 13 mL of water, followed by 59 mL of 25% aqueous sodium hydroxide solution. The resulting mixture is stirred at room temperature for 2 hours, filtered through celite, and concentrated in vacuo. The title compound is obtained (90.40 g) as a light yellow oil (silica; $R_f$=0.2; 1% methanol, 99% chloroform).

Step D: Preparation of 3-[(3,6-Dihydro-4-phenyl-1(2H)-pyridinyl)methyl]cyclohexanone A solution of 1-(1,4-dioxaspiro[4.5]dec-7-ylmethyl)-1,2,3,6-tetrahydro-4-phenylpyridine (Step C) (90.4 g) in 500 mL of acetone and 500 mL of 10% aqueous hydrochloric acid solution is refluxed, under nitrogen, for 3 hours. The solvent is evaporated in vacuo and partitioned into ethyl acetate/dilute ammonium hydroxide solution. The organic extract is dried over magnesium sulfate and concentrated, leaving the title compound (68.9 g) as a light pink solid; mp 56°-59° C. Mass spectrum (MS) electron ionization (EI) 269 (m, 41%), 172 (100%).

EXAMPLE B

3-[[4 (2-Pyridinyl)piperazinyl]methyl]cyclohexanone

Step A: Preparation of 1-(1,4-Dioxaspiro[4.5]dec -7-ylcarbonyl)-4-(2-pyridinyl)piperazine From 1,4-dioxaspiro[4.5]decane-7-carboxylic acid (Example A, Step A) (10 g), triethylamine (8 g), isobutyl chloroformate (7.9 g) and 1-(2-pyridyl)piperazine (8.3 g) using the procedure of Example A, Step B is obtained 9.8 g of the title compound as an oil.

Step B: Preparation of 1-(1,4-Dioxaspiro[4.5]dec-7-ylmethyl)-4-(2-pyridinyl)perazine From aluminum chloride (5.39 g), lithium aluminum hydride (4.61 g) and 1-(1,4-dioxaspiro[4.5]dec-7-ylcarbonyl)-4-(2-pyridinyl)piperazine (40.22 g) (Step A) using the procedure of Example A, Step C is obtained 35.66 g of the title compound as an oil.

Step C: Preparation of 3-[[4(2-Pyridinyl)piperazinyl]-methyl]cyclohexanone

From 1-(1,4-dioxaspiro[4.5]dec-7-ylmethyl)-4-(2-pyridinyl)piperazine (Step B) (8.4 g) and 50 mL of 10% aqueous hydrochloric acid solution using the procedure of Example A, Step D is obtained 6.4 g of the title compound as a white solid; mp 86°-90° C.

EXAMPLE C (R)-1,2,3,6-Tetrahydro-4-phenyl-1-[(3-oxocyclohexane)methyl]pyridine Dicyclohexylcarbodiimide (41.53 g) in dichloromethane (400 mL) is added to (R)-3-oxocyclohexanecarboxylic acid, brucine salt (Numata, A., et al, *Yakugaku Zasshi*, Part 2(1):1298-1305 (1968)) (98.22 g), 1,2,3,6-tetrahydro-4-phenylpyridine hydrochloride (39.39 g), hydroxybenzotriazole hydrate (27.20 g), and triethylamine (28.07 g) in dichloromethane (1000 mL) and stirred overnight. The mixture is filtered and evaporated to a brown solid. This solid is slurried in ethyl acetate (1000 mL), filtered, washed with 2N hydrochloric acid (2×500 mL), 2N sodium carbonate (500 mL), brine (500 mL), dried over magnesium sulfate, filtered, and evaporated to leave 55.87 g of an oil. This oil is stirred in dichloromethane (150 mL) with 2-methoxy-1,3-dioxolane (40 mL) and methanesulfonic acid (1 mL) at room temperature for 3 days. The mixture is washed with 2N sodium carbonate (150 mL), dried over magnesium sulfate, filtered, and evaporated to leave a yellow oil. This oil is dissolved in tetrahydrofuran (200 mL) and added to lithium aluminum hydride (7.48 g) in tetrahydrofuran (200 mL) pretreated with aluminum trichloride (8.76 g) in ether (100 mL) at 0° C., and stirred at 0° C. for 2 hours. Water (2 mL) and 25% sodium hydroxide (10 mL) are added and the mixture is filtered and evaporated. The residue was heated to reflux in acetone (300 mL) and 2N hydrochloric acid (300 mL) for 6 hours. The solvent is mostly evaporated and the residue treated with 2N sodium carbonate (500 mL). The mixture is extracted with dichloromethane (3×300 mL), the extracts dried over magnesium sulfate, filtered, and evaporated. The residue is purified by column chromatography on silica gel (250 g TLC grade) eluting with 50% ethyl acetate/hexane to give a yellow wax (39.40 g). Rotation +15.2° (c=1.00, methanol).

EXAMPLE D (R)-3-phenyl-3-cyclohexenecarboxylic acid
Step A: Preparation of ethyl tetrahydro-2-oxo-2H-pyran-3-carboxylate Sodium metal (3.0 g) is dissolved in absolute ethanol (60 mL) under nitrogen and the solution is concentrated under vacuum. Diethyl carbonate (50 mL) and δ-valerolactone (11.5 g) are added to the solid sodium ethoxide and the solution is heated on an oil bath at 130° C. Ethanol is distilled off through a 2-two inch vigreux column at 80°-95° C. during 30 minutes (15 mL collected). The oil bath temperature is then increased to 150° C. and distillate (11 mL) is collected up to 120° C. A solid forms during the distillation. The reaction mixture is cooled and diluted with diethyl ether (100 mL). The mixture is filtered and the solid residue is washed with ether. The solid residue is stirred with water (80 mL) and acetic acid (8 mL) and the mixture is extracted with diethyl ether (100 mL). The extract is dried over magnesium sulfate and concentrated to afford an oil (13.1 g). Short path vacuum distillation gives ethyl tetrahydro-2-oxo-2H-pyran-3-carboxylate (9.1 g), bp 115°-118° C. (0.5 mm/Hg).
Step B: Preparation of 3-(benzoylmethyl)tetrahydro-2H-pyran-2-one Ethyl tetrahydro-2-oxo-2H-pyran-3-carboxylate (4.32 g) in tetrahydrofuran (10 mL) is added dropwise to sodium hydride (1.0 g of 60% dispersion in oil, washed with hexane) suspended in tetrahydrofuran (10 mL) with stirring under nitrogen. The mixture is stirred until gas evolution (almost) ceases, then 2-bromoacetophenone (4.98 g, kugelrohr distilled prior to use) in tetrahydrofuran (10 mL) is added, and the mixture is heated on an oil bath at 65° C. for 2.5 hours. (NOTE: exotherm occurs with some material boiling up into the condenser. Wait for initial reaction to subside before heating.) The cooled mixture is partitioned between diethyl ether (150 mL) and dilute aqueous potassium carbonate (100 mL, ~3%). The ether layer is washed with 10% aqueous potassium carbonate, water, saturated aqueous sodium chloride, and dried over magnesium sulfate. The solvent is removed under vacuum to afford an orange-red oil (6.58 g). The oil (6.17 g) is stirred with tetrahydrofuran (50 mL) and 1M hydrochloric acid (50 mL) and heated to reflux on an oil bath at 79° C. for 49 hours. The tetrahydrofuran is removed under vacuum and the residue is extracted with dichloromethane (2×50 mL). The extract is dried over magnesium sulfate and concentrated under vacuum to afford an oil (5.70 g) which is crystallized from 1:1 hexane:ethyl acetate (30 mL). The crystals are filtered off, washed with 1:1 hexane:ethyl acetate, and hexane and vacuum dried to give 2.59 g of 3-(benzoylmethyl)tetrahydro-2H-pyran-2-one as a white solid; mp 93°-94° C.
Step C: Preparation of 3-phenyl-3-cyclohexenecarboxylic acid 3-(Benzoylmethyl)tetrahydro-2H-pyran-2-one (4.05 g) and triphenylphosphonium hydrobromide (6.38 g) are thoroughly mixed and heated under nitrogen with stirring on an oil bath at 170° C. for 2 hours. Upon cooling, the glassy solid is powdered and dissolved in dry dimethylsulfoxide (50 mL) and dry tetrahydrofuran (30 mL) is added. The solution is cooled to 10° C. and stirred under nitrogen while dimsyl sodium in dimethylsulfoxide (18.6 mL of 2M, prepared by dissolving sodium hydride in dimethylsulfoxide at 80° C. over 1 to 2 hours) is added dropwise at <18° C. The solution is stirred at 25° C. for 2 hours, then the dimethylsulfoxide is distilled off under vacuum at up to 80° C. The residue is partitioned between dichloromethane (100 mL) and water (100 mL) containing potassium carbonate (2 g). The aqueous layer is washed with dichloromethane (50 mL), then acidified with concentrated hydrochloric acid and extracted with dichloromethane (2×70 mL). The extract is dried over magnesium sulfate and concentrated under vacuum to afford an oil (3.76 g). The oil is washed through silica gel (25 g) with 1:1 chloroform:ethyl acetate and concentrated to give a solid (2.56 g). Trituration of this material from a minimum of tetrahydrofuran by addition of hexane (30 mL) gave 2.02 g of 3-phenyl-3-cyclohexenecarboxylic acid as a white solid; mp 111°-112° C. Additional material (0.45 g; mp 107°-111° C.) is obtained upon concentrating the supernatant solution to 5 mL.
Step D: Resolution of 3-phenyl-3-cyclohexenecarboxylic acid 3-Phenyl-3-cyclohexenecarboxylic acid (8.1 g, Step C) is dissolved in 2-butanone (20 mL) and (S)-α-methylbenzylamine (4.85 g) in 2-butanone (10 mL) added. The salt precipitates and more 2-butanone (200 mL) is added and the mixture heated to dissolve the salt. The salt recrystallizes on cooling to 25° C. and it is collected and dried to give 10.02 g of the salt. The salt is recrystallized 5 times from 2-butanone to give 3.14 g of a white powder. The powder is slurried in ethyl acetate and washed with 2N hydrochloric acid. The ethyl acetate layer is dried over magnesium sulfate, filtered, and evaporated to give (R)-3-phenyl-3-cyclohexenecarboxylic acid as a white powder; mp 77°–80° C.

EXAMPLE E 3-phenyl-3-cyclopentenecarboxylic acid

Step A: Preparation of 3-(benzoylmethyl)-4,5-dihydro-2(3H)-furanone

Mandelonitrile (66.5 g) is stirred with 1M hydrochloric acid (0.20 mL) at 50° C. while ethyl vinyl ether (55 mL) is added over 2 hours. The mixture is then heated at 80° C. for 2 hours. The mixture is fractionally distilled (kugelrohr) and the fraction distilling at 100°–120° C./0.8 mmHg collected to give 74.8 g of a colorless oil. A portion (10.5 g) is stirred in tetrahydrofuran (125 mL) and cooled in a dry ice/acetone bath under nitrogen. n-Butyllithium (33 mL of 1.6M in hexanes) is added dropwise, keeping the internal temperature below −65° C. The mixture is stirred for 15 minutes and α-methylene-γ-butyrolactone (5.08 g) in tetrahydrofuran (20 mL) is added, keeping the internal temperature below −64° C. The mixture is stirred for 30 minutes and warmed to −50° C. Saturated aqueous ammonium chloride (100 mL) is added and the mixture stirred for 5 minutes. The mixture is extracted with ether (2×200 mL), the extracts dried over magnesium sulfate, filtered, and evaporated. The residue is stirred in ethanol (45 mL) with 5% sulfuric acid (12 mL) for 20 minutes. Water (250 mL) is added and the mixture extracted with chloroform (3×100 mL), the extracts dried over magnesium sulfate, filtered, and evaporated. The residue is heated to 140° C. for 40 minutes and kugelrohr distilled at 120°–180° C./1 mmHg to give 8.61 g of an oil which solidified on standing. This solid is recrystallized from ethyl acetate/hexane to give 6.27 g of 3-(benzoylmethyl)-4,5-dihydro-2(3H)-furanone; mp 77°–79° C.

Step B: Preparation of 3-phenyl-3-cyclopentenecarboxylic acid 3-(Benzoylmethyl)-4,5-dihydro-2(3H)-furanone (5.00 g, Step A) and triphenylphosphine hydrobromide (8.41 g) are mixed and heated to 170° C. in an oil bath under nitrogen for 1 hour. The mixture is cooled and powdered. The powder is dissolved in dimethylsulfoxide (50 mL) and diluted with tetrahydrofuran (30 mL). The solution is stirred under nitrogen and cooled in an ice-bath. Dimsyl sodium (25 mL of 2M, see Example D, Step C) is added dropwise over 20 minutes keeping the internal temperature below 14° C. The mixture is stirred at 25° C. for 2 hours and the solvents evaporated. The residue is treated with water (80 mL) containing saturated aqueous sodium bicarbonate (10 mL) and extracted with dichloromethane (3×50 mL). The extracts are washed with dilute aqueous sodium bicarbonate. The aqueous layers are washed with dichloromethane (30 mL) and acidified with concentrated hydrochloric acid. The aqueous layers are extracted with dichloromethane (3×50 mL), the extracts dried over magnesium sulfate, filtered, and evaporated to a brown oil. The oil is washed through silica gel (30 g) with 2:1 chloroform:ethyl acetate to give 3.1 g of 3-phenyl-3-cyclopentenecarboxylic acid as a brown solid.

We claim:

1. A compound of Formula I

Z—CH$_2$—Y         I wherein Z is

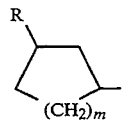

wherein R is aryl, 2-, 3-, or 4-pyridinyl or 2-, 3-, or 4-pyridinyl substituted by lower alkyl, lower alkoxy, hydroxy, or halogen, 2-, 4-, or 5-pyrimidinyl or 2-, 4-, or 5-pyrimidinyl substituted by lower alkyl, lower alkoxy, hydroxy, or halogen, 2- or 3-thienyl or 2- or 3-thienyl substituted by lower alkyl or halogen, 2- or 3-furanyl or 2- or 3-furanyl substituted by lower alkyl or halogen, and m is an integer of 1, 2, or 3,

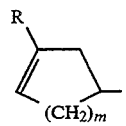

wherein R and m are as defined above,

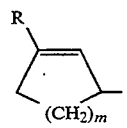

wherein R and m are as defined above, or

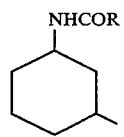

wherein R is as defined above;

Y is

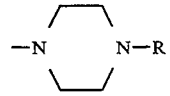

wherein R is as defined above; and corresponding isomers thereof; or a pharmaceutically acceptable acid addition salt thereof.

2. A compound according to claim 1, in which

R is phenyl, phenyl substituted by lower alkyl, lower alkoxy, lower dialkoxy, halogen, hydroxy, dihydroxy, amino, lower alkyl amino, lower dialkyl amino, 2- or 3-pyridyl, 2- or 3-pyridyl substituted by lower alkyl, lower alkoxy, or halogen, 2- or 3-thienyl, 2- or 3-thienyl substituted by lower alkyl, lower alkoxy, or halogen, 2-, 3- or 5-pyrimidinyl, or

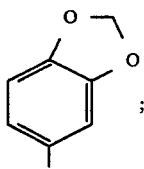

m is an integer of 1 or 2; and Y is

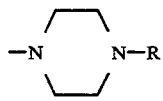

wherein R is as defined above.

3. A compound according to claim 2, in which

R is phenyl, phenyl substituted by para-halogen, para-methoxy, ortho or para lower alkyl, para mono- or di-lower alkyl amino, 2- or 3-pyridyl, 2- or 3-thienyl, 5-pyrimidinyl, or

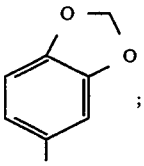

m is an integer of 2; and Y is

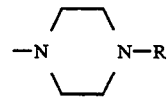

wherein R is as defined above.

4. A compound according to claim 3 selected from the group consisting of:

(±)-1-[(3-Phenyl-3-cyclohexen-1-yl)methyl]-4-(2-pyridinyl)piperazine;

(±)-1-[(3-Phenyl-2-cyclohexen-1-yl)methyl]-4-(2-pyridinyl)piperazine;

(±)-1-[[3-(4-Fluorophenyl)-3-cyclohexen-1-yl]methyl]-4-(2-pyridinyl)piperazine;

(±)-1-[[3-(4-Fluorophenyl)-2-cyclohexen-1-yl]methyl]-4-(2-pyridinyl)piperazine;

(R)-1-[(3-Phenyl-3-cyclohexen-1-yl)methyl]-4-(2-pyridinyl)piperazine;

(±)-1-Phenyl-4-[(3-phenyl-3-cyclohexen-1-yl)methyl]piperazine dihydrochloride;

(±)-2-[4-[[3-phenyl-3-cyclohexen-1-yl)methyl]-1-piperazinyl]pyrimidine; and (±)-1-[(3-phenyl-3-cyclopenten-1-yl)methyl]-4-(2-pyridinyl)piperazine.

5. A method of treating schizophrenia comprising administering to a host suffering therefrom a therapeutic effective amount of a compound according to claim 1 in unit dosage form.

6. A pharmaceutical composition adapted for administration as a dopaminergic, antipsychotic, or antihypertensive agent comprising a therapeutic effective amount of a compound according to claim 1 in admixture with a pharmaceutically acceptable excipient, diluent, or carrier.

* * * * *